(12) United States Patent
Kato

(10) Patent No.: US 8,961,938 B2
(45) Date of Patent: *Feb. 24, 2015

(54) DENTIFRICE COMPOSITION

(75) Inventor: Kazuhiko Kato, Sumida-ku (JP)

(73) Assignee: Kao Corporation, Tokyo (JP)

( * ) Notice: Subject to any disclaimer, the term of this patent is extended or adjusted under 35 U.S.C. 154(b) by 2337 days.

This patent is subject to a terminal disclaimer.

(21) Appl. No.: 11/512,326

(22) Filed: Aug. 30, 2006

(65) Prior Publication Data

US 2007/0059256 A1  Mar. 15, 2007

(30) Foreign Application Priority Data

Sep. 5, 2005 (JP) .................. 2005-257103
Sep. 5, 2005 (JP) .................. 2005-257104
Sep. 5, 2005 (JP) .................. 2005-257105
Sep. 5, 2005 (JP) .................. 2005-257106

(51) Int. Cl.
A61K 8/73 (2006.01)
A61K 8/33 (2006.01)
A61K 8/34 (2006.01)
A61Q 11/00 (2006.01)

(52) U.S. Cl.
CPC .............. *A61K 8/345* (2013.01); *A61Q 11/00* (2013.01)
USPC ........................................................ 424/49

(58) Field of Classification Search
USPC ........................................................ 424/49
See application file for complete search history.

(56) References Cited

U.S. PATENT DOCUMENTS

| | | | |
|---|---|---|---|
| 4,140,757 A * | 2/1979 | Wason et al. ................... | 424/49 |
| 5,698,327 A | 12/1997 | Persello | |
| 5,882,631 A * | 3/1999 | Suga et al. ....................... | 424/49 |
| 5,973,212 A * | 10/1999 | De Sadeleer et al. ......... | 568/852 |
| 6,238,648 B1 * | 5/2001 | Leusch et al. ................... | 424/49 |

FOREIGN PATENT DOCUMENTS

| | | |
|---|---|---|
| CN | 1080843 A | 1/1994 |
| EP | 0 430 663 A1 | 6/1991 |
| EP | 1 721 599 A1 | 11/2006 |
| JP | 50-12242 | 2/1975 |
| JP | 10-306048 | 11/1998 |
| JP | 10-337154 | 12/1998 |
| JP | 11-49653 | 2/1999 |
| JP | 11-100314 | 4/1999 |
| JP | 2000-191483 | 7/2000 |
| JP | 2000-191484 | 7/2000 |
| JP | 2004-238321 | 8/2004 |
| JP | 2005-8579 | 1/2005 |
| JP | 2005-29484 | 2/2005 |
| JP | 2005-62137 | 3/2005 |
| JP | 2007-63188 | 3/2007 |
| WO | WO 99/51196 | 10/1999 |
| WO | WO 01/64168 A2 | 9/2001 |
| WO | WO 2004/105680 A2 | 12/2004 |
| WO | 2005/084624 * | 3/2005 |

OTHER PUBLICATIONS

Japanese Industrial Standard, K 5101-13-2; 2004.
Fuji Sylysia, pamphlet of Sylysia®.
U.S. Appl. No. 10/589/658, filed Aug. 16, 2006, Katou, et al.
Office Action issued Aug. 31, 2010, in Japan Patent Application No. 2005-251545 (with English-language translation).
Office Action issued Sep. 28, 2010, in Japanese Patent Application No. 2005-257103 with English translation.
Office Action issued Sep. 28, 2010, in Japanese Patent Application No. 2005-257104 with English translation.
Office Action issued Sep. 28, 2010, in Japanese Patent Application No. 2005-257105 with English translation.
Office Action issued Sep. 28, 2010, in Japanese Patent Application No. 2005-257106 with English translation.
Office Action issued Feb. 8, 2011, in Japanese Patent Application No. 2005-257107 (with English Translation).

* cited by examiner

*Primary Examiner* — Lezah Roberts
(74) *Attorney, Agent, or Firm* — Oblon, Spivak, McClelland, Maier & Neustadt, L.L.P.

(57) ABSTRACT

Provided is a dentifrice composition containing erythritol, which is excellent in storage stability and the persistence of a cool feeling and gives a higher refreshing feeling. The dentifrice composition comprises:

(A) 15 to 50 weight % of erythritol having a particle size of less than 355 μm;
(B) 10 to 40 weight % of water; and
(C) 0.6 to 3 weight % of a binder.

19 Claims, No Drawings

DENTIFRICE COMPOSITION

CROSS REFERENCES TO RELATED APPLICATIONS

This application claims priority to Japanese Patent Application No. 2005-257103, filed on Sep. 5, 2005, Japanese Patent Application No. 2005-257104, filed on Sep. 5, 2005, Japanese Patent Application No. 2005-257105, filed on Sep. 5, 2005, and Japanese Patent Application No. 2005-257106, filed on Sep. 5, 2005.

FIELD OF THE INVENTION

The present invention relates to a dentifrice composition containing an erythritol.

BACKGROUND OF THE INVENTION

In general, the purpose for brushing teeth resides in making the oral cavity clean and bringing a refreshing feeling to the same. A perfume component, which is commonly blended in a dentifrice composition, is an essential component needed for providing a refreshing feel. In recent years, however, there has been an increasing to have an oily meal and a more spicy meal, so that a dentifrice composition capable of imparting a higher refreshing feel is desired.

To improve the refreshing feel, there is known method, e.g., a method of increasing the quantity of the perfume component, or a method of adding a solvent such as ethanol. Yet there has been a problem that increasing the concentration of said components to the composition becomes strongly stimulating in the oral cavity and suppresses foaming, and therefore they could also impair a sense of use upon the teeth brushing.

Accordingly, a dentifrice composition is desired that can generate a higher refreshing feel without increasing the blending quantity of the perfume and the solvent such as ethanol.

JP-A-2000-191483 discloses a dentifrice composition excellent in a refreshing feel, wherein the composition contains a component causing an endothermic hydration reaction such as erythritol and has a water content of 10 weight % or less. However, said composition has problems with storage stability, in part because its water-soluble polymer blended as a binder does not sufficiently dissolve due to the low content of water and therefore there is a phenomenon such that water and other liquid components exude from the system over time. Furthermore, no plain cool feeling in the oral cavity has yet been obtained, even though slightly possible to obtain.

DISCLOSURE OF THE INVENTION

The present invention provides a dentifrice composition containing:

(A) 15 to 60 weight % of erythritol having a particle size of less than 355 μm;
(B) 10 to 40 weight % of water; and
(C) 0.6 to 3 weight % of a binder.

The present invention also provides a dentifrice composition adding:

(A) 20 to 60 weight % of erythritol having a particle size of less than 355 μm;
(B) 10 to 40 weight % of water; and
(C) 0.6 to 3 weight % of a binder.

An object of the invention is to provide a dentifrice composition containing erythritol, excellent in the storage stability and the persistence of cool feeling and giving a higher refreshing feel.

As the result of first studying a method for enhancing a refreshing feel and a cool feeling during brushing teeth, the present inventor has found that the refreshing feel and the cool feeling can be improved by adding erythritol having a particular particle size and further controlling the content thereof and the water content in the composition. However, the separation phenomenon of water and other liquid components has occurred because the water content in the composition is limited, and the storage stability has therefore been less than sufficient. Then, the inventor has found that a highly storage stability is achieved by controlling the blending quantity and type of the binder used.

The dentifrice composition according to the invention is excellent in the storage stability and gives a high refreshing feel when applied to the oral cavity because a cool feeling is long maintained.

The dentifrice composition of the invention is characterized in that the composition contains erythritol (component (A)) having a particle size of less than 355 μm. Typically available erythritol is a crystalline erythritol produced by fermenting glucose before recrystallization, and has a particle size larger than that of the present invention. Thus, such erythritol obtained is preferably pulverized to control the particle size thereof for use in the dentifrice composition of the invention.

For pulverizing the erythritol, for example, a roller mill, a hammer mill, a high-speed pulverizer, or a pulverizer is generally used; however, pulverization using the high-speed pulverizer or the hammer mill is preferable because they enable a particle size to be easily controlled and are excellent in production efficiency.

In addition, although the structure of erythritol is present in the forms of the three isomers L-erythritol, D-erythritol, and meso-erythritol, the erythritol according to the invention may have any of these structures. The crystalline erythritol is commercially available from, for example, Nikken Chemicals Co., Ltd., Mitsubishi-Kagaku Foods Corporation, and Cerestar Inc.

The particle size of erythritol is less than 355 μm because the refreshing feel and the cool feeling are achieved; however, 3 μm to less than 355 μm is preferable. In view of a persistent cool feeling in the mouth, it is preferably 45 μm to less than 355 μm, more preferably 45 μm to less than 300 μm, and even more preferably 45 μm to less than 250 μm.

In this regard, the particle size of erythritol is determined as described below.

Sieve: JIS Standard Sieves φ75 mm

Opening: A receiver is placed below sieves having openings of 500 μm, 355 μm, 250 μm, 180 μm, 125 μm, 90 μm, and 45 μm in order from the top stage.

Shaker: Micro electromagnetic shaker Model M-2 (Tsutsui Scientific Instruments Co., Ltd.)

Method: On the 500 μm sieve is placed 15 g of sample, followed by classification using the electromagnetic shaker for 5 minutes. Total erythritol present on the sieves having openings of 250 μm, 180 μm, 125 μm, 90 μm, and 45 μm is defined as erythritol having a particle size of 45 μm to less than 355 μm.

The distribution of particle sizes of less than 45 μm can be determined using a dry laser distribution diffraction particle size analyzer.

In view of achieving a high refreshing feel, the content of erythritol with a particle size of less than 355 μm in the dentifrice composition of the invention is 15 to 60 weight %, is preferably 20 weight % or more, more preferably 25 weight % or more, and even more preferably 30 weight % or more; the upper limit of the content is preferably 55 weight % or less, and more preferably 50 weight % or less.

Thus, the blending quantity of the erythritol in the composition with a particle size of less than 355 μm is 20 to 60 weight %, but preferably 25 weight % or more, more preferably 30 weight %, and even more preferably 35 weight %; the upper limit of the blending quantity is preferably 55 weight % or less.

In view of achieving good storage stability and a higher refreshing feel and a cool feeling, the content of water (component (B)) in the dentifrice composition of the invention is 10 to 40 weight %, preferably 12 to 35 weight %, more preferably 15 to 30 weight %, and even more preferably 18 to 25 weight %.

Binder (component (C)) used in the invention is one or more water-soluble polymers selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, acacia gum, guar gum, karaya gum, locust bean gum, gellan gum, tamarind gum, psyllium sead gum, polyvinyl alcohol, sodium chondroitin sulfate, and methoxyethylene-maleic anhydride copolymer.

In view of storage stability, the content of the binder in the dentifrice composition of the invention is 0.6 to 3 weight %, preferably 0.7 to 2 weight %, and more preferably 0.8 to 1.2 weight %. Less than 0.6 weight % is not sufficient in terms of the stability, while more than 3 weight % increases the viscosity of the composition and therefore impairs the refreshing feeling.

The use of at least sodium carboxymethylcellulose, particularly with a degree of etherification of 0.8 to 1.5 as a binder is preferable in that the storage stability of the dentifrice composition is further improved. The degree of etherification of the sodium carboxymethylcellulose is preferably 0.8 to 1.3, and more preferably 0.8 to 1.0. An excessive degree of etherification is liable to pose a problem with the dispersibility and stringiness of a paste in the dentifrice composition because the aqueous solution thereof becomes more viscous, while an insufficient degree of etherification is unfavorable because a liquid separation during in storage occurs owing to the reduced solubility thereof in water. Here, "degree of etherification" refers to the number per glucose unit of carboxymethyl groups substituted for the hydroxyl groups of cellulose.

In addition, in view of improving stability, the carboxymethylcellulose preferably has a 1% aqueous solution viscosity of 50 cps or less, preferably 30 cps or less, and even more preferably 5 to 20 cps. Here, the aqueous solution viscosity is a viscosity determined at 25° C. and 60 revolutions using a B-type viscometer. Such sodium carboxymethylcellulose is available as CMC Daicel (Daicel Chemical Industries, Ltd.), Sunrose (Nippon Paper Chemicals Co., Ltd.), Cellogen (Daiichi Kogyo Seiyaku Co., Ltd.), or Cekol (Noviant).

In view of a storage stability, the content of sodium carboxymethylcellulose in the dentifrice composition of the invention is 0.05 to 2 weight %, preferably 0.1 to 1.5 weight %, and more preferably 0.2 to 1 weight %.

The use of at least xanthan gum as a binder is also preferable in terms of a storage stability and foaming. According to the invention, the molecular weight and molecular weight distribution of xanthan gum is not restricted, provided that the gum is used as a binder for dentifrice agents. In view of suppressing a reduction in the viscosity of foam and achieving elastic foam, the content of xanthan gum in the dentifrice composition of the invention is 0.01 to 0.5 weight %, preferably 0.02 to 0.3 weight %, and more preferably 0.03 to 0.2 weight %.

The dentifrice composition of the invention may be blended of 0.5 to 10 weight % of thickening silica (component (D)) having an oil absorption capacity of 200 to 400 mL/100 g. The thickening silica (component (D)) used in the invention is a component having a thickening effect, and has an oil absorption capacity of 200 to 400 mL/100 g, preferably 220 to 380 mL/100 g, and more preferably 250 to 350 mL/100 g in view of improving the stability of the composition. Here, "oil absorption capacity" refers to the amount of an oil which a silica can support, and a method for determination thereof is according to JIS K5101 (ISO 787-5). Kneading is carried out by a kneading method using a spatula while dropwise adding a purified linseed oil, and a time when the paste has reached smooth hardness is defined as a final point to measure the amount of the linseed oil used. The silica is available as Sylysia or Sylopure (Fuji Silysia Chemical Ltd.), Tixosil (Rhodia Co., Ltd.), Sorbosil (Ineos Silicas Ltd.), Finesil (Tokuyama Corporation), or Nipgel (Tosoh Silica Corporation). In this respect, the silica having a high oil absorption capacity used here differs from the silica used as an abrasive.

In view of a storage stability, the content of the silica (component (D)) in the dentifrice composition of the invention is 0.5 to 10 weight %, preferably 1 to 8 weight %, more preferably 1.2 to 7 weight %, and even more preferably 1.5 to 5 weight %.

In addition, the combination of the above-described binder (C) and the silica (D) further improves the storage stability of the dentifrice composition of the invention.

Further, according to the dentifrice composition of the invention, a polishing powder (E) is blended to achieve an excellent tooth-cleaning effect as well as an enhanced refreshing feel and a cool feeling due to erythritol.

In view of achieving a sufficient cleaning effect, the polishing powder (E) is preferably contained at 5 to 20 weight %, preferably 8 to 18 weight %, and more preferably 10 to 15 weight % in the dentifrice composition of the invention.

The polishing powder (E) may be used is, for example, a silica-based abrasive such as hydrated silica, anhydrous silica, silica gel, aluminosilicate, or zirconosilicate, calcium secondary phosphate dihydrate or nonhydrate, calcium pyrophosphate, calcium carbonate, alumina, aluminum hydroxide, magnesium acetate, magnesium tertiary phosphate, or zeolite. In view of a cleaning effect and safety, hydrated silica, anhydrous silica, calcium hydrogenphosphate dihydrate, calcium hydrogenphosphate nonhydrate, alumina, aluminum hydroxide, calcium carbonate, or zeolite is preferred.

The above-described polishing powder (E) is preferably used in the form of a combination of a polishing powder from the group consisting of such powders having a small particle size and a large RDA (E1) and a polishing powder from the group consisting of such powders having a larger particle size and a smaller RDA relative to those of E1 (E2). The combination of such polishing powders having different physical properties achieves an excellent tooth-cleaning effect in a reduced amount of powder. The polishing powder (E1) has an average particle size of 1 to 10 μm, preferably 2 to 8 μm, and more preferably 3 to 6 μm, and an RDA value of 150 to 300, preferably 180 to 250. The polishing powder (E2) has an average particle size of 5 to 20 μm, preferably 6 to 18 μm, more preferably 8 to 15 μm, and an RDA value of 50 to 150, preferably 80 to 120. Here, RDA (Radioactive Dentin Abration) is a measure of the polishing power of toothbrushing for the dentin, and determined by an RDA test (Hefferen, Journal of Dental Research 1976, No. 7, 8: p. 563-573).

In addition, the polishing powder (E1) and polishing powder (E2) may be used in any form of a combination of the same components and a combination of different components. The blending ratio of the polishing powder (E1) to the polishing powder (E2) is 50:50 to 5 to 95, and preferably 40:60 to 10:90.

In addition to the above-described components, the dentifrice composition of the invention may properly contain, for example, a foaming agent, a foaming assistant, a wetting agent, a sweetening agent, a preservative, an enzyme, a pH adjustor, a bactericide, a medicinal component, a pigment, a dye, and a perfume. It may also contain erythritol having another particle size (355 μm or more). In this case, the average size of total erythritol particles contained or blended in the composition is preferably 200 μm or less, more preferably 30 to 150 μm.

The foaming agent may be an anionic surfactant represented by a sodium alkylsulfate. The alkyl group of the sodium alkylsulfate has a carbon number of 8 to 18, preferably 10 to 16, more preferably 12 to 14, and sodiumalkylsulfates having alkyl groups having these carbon numbers may be used in an arbitrary proportion. In view of foaming properties and irritation to the oral cavity, the content of sodium alkylsulfate in the dentifrice composition of the invention is preferably 0.5 to 2 weight %, more preferably 0.8 to 1.8 weight %, and even more preferably 1 to 1.5 weight %.

The combination of sodium alkylsulfate and xanthan gum as a binder is preferable because it provides a dentifrice composition excellent in foaming and foam stability.

A nonionic surfactant may be further added to the dentifrice composition of the invention in order to improve a foaming efficacy. Examples of the nonionic surfactant include polyglycerol fatty acid esters, sucrose fatty acid esters, sorbitan fatty acid esters, polyoxyethylene higher alcohol ethers, polyoxyethylene fatty acid esters, alkylglucosides, and polyoxyethylene-polyoxypropylene copolymers. One or more nonionic surfactants selected therefrom may be added, and the content of these nonionic surfactants in the dentifrice composition is 0.1 to 2 weight %, more preferably 0.2 to 1.5 weight %, and even more preferably 0.3 to 1 weight %.

The suitable wetting agent used is, for example, glycerin, sorbitol, propylene glycol, polyethylene glycol, xylitol, maltit, lactit, or trehalose.

Examples of the sweetening agent include saccharine sodium, aspartame, thaumatin, acesulfame potassium, stevioside, stevia extract, p-methoxycinnamic aldehyde, neohesperidyl dihydrochalcone, and perillartine.

Examples of the perfume agent and essential oil include 1-menthol, carvone, anethole, eugenol, limonene, peppermint oil, spearmint oil, ocimene, n-amyl alcohol, citronellol, α-terpineol, methyl salicylate, methyl acetate, citroneol acetate, cineol, linalool, ethyllinalool, vanillin, thymol, lemon oil, orange oil, sage oil, rosemary oil, cinnamon oil, pimento oil, shiso oil, clove oil, and eucalyptus oil.

In addition, examples of various other active ingredients include water-soluble phosphate compounds such as potassium orthophosphate and sodium orthophosphate; anti-inflammatory agents such as chlorohydroxyaluminiumallantoinate, azulene, glycyrrhetic acid, epidihydrocholesterin, α-bisabolol, and glycyrrhizic acid and its salts; phenolic compounds such as hinokitiol; antiplasmin agents such as tranexamic acid and epsilon aminocaproic acid; vitamin E derivatives such as dl-tocopherol acetate; copper compounds such as sodium copperchlorophyllin and copper gluconate; salts such as sodium chloride and potassium nitrate; bactericides such as triclosan, cetylpyridinium chloride, benzethonium chloride, chlorhexidine salts, and trichlorocarbanilide; enzymes such as dextranase, mutanase, amylase, and lysozyme chloride; extracts such as japanese angelica root, phellodendron bark, clove, rosemary, scutellaria root, and safflower extracts; aluminium lactate, strontium chloride, berberine, hydroxamic acid and its derivatives, sodium tripolyphosphate, zeolite, polyvinyl pyrrolidone, dihydrocholesterol, and zinc citrate.

In view of achieving a higher refreshing feel, the dentifrice composition of the invention desirably has erythritol dispersed in a powder state. For that purpose, it is preferred that erythritol is introduced directly in the form of powder into the final step of production. The use of such a production process enables erythritol to be present in a powder state in the dentifrice composition that the powdery erythritol little dissolves in water. By way of specific example, components such as purified water, a wetting agent, a binder, a flavoring agent, a preservative, an abrasive, a foaming agent, a sweetening agent, and a medicinal ingredient can be weighed at formulation amounts, then mixed the purified water, the binder, and other components such as the wetting agent according to a given conditions of production to sufficiently swell the binder, followed by adding the abrasive, foaming agent, flavoring agent, and powdery erythritol for defoam mixing to produce the dentifrice composition of the invention.

The viscosity (Helipath viscometer, rotor C, 2.5 r/min for one minute) of the dentifrice composition of the invention at 25° C. is preferably 1,500 to 5,000 dPa·s, more preferably 2,000 to 4,500 dPa·s, and even more preferably 2,500 to 4,000 dPa·s.

DETAILED DESCRIPTION OF THE PREFERRED EMBODIMENTS

Examples

Examples 1 to 3 and Comparative Examples 1 to 2

Preparation of Dentifrice Compositions

The dentifrice compositions of Examples 1 to 3 and Comparative Examples 1 to 2 were prepared according to the compositions shown in Table 1. Purified water, a binder, and other components such as a wetting agent, a sweetening agent, and a medicinal ingredient were mixed according to a given conditions of production until swelling the binder sufficiently, followed by adding an abrasive, a foaming agent, a flavoring agent, and, lastly, erythritol for defoam mixing.
(1) Evaluation of Storage Stability The dentifrice compositions shown in Table 1 were each filled in a dentifrice tube for storage and stored at 5° C., room temperature, or 40° C. for 3 months. Then, the tube was cut open to evaluate whether or not a liquid component was separated from the dentifrice, using the following criteria.
<Evaluation Criteria for Storage Stability>
  Excellent: No separation of liquid is observed.
  Good: A slight separation of liquid is observed.
  Poor: An apparent separation of liquid is observed.
(2) Evaluation of Cool Feeling
  Ten subjects (5 men and 5 women) placed 1 g of dentifrice composition on a toothbrush and freely performed the brushing for about 2 minutes, and evaluated a cool feeling using the following criteria.

<Evaluation Criteria for Cool Feeling>
  Excellent: A cool feeling persists long.
  Good: A cool feeling persists somewhat long.
  Poor: A cool feeling is not sensed, or disappears rapidly.

(1) Evaluation of a Refreshing Feel and a Cool Feeling
  Ten subjects (5 men and 5 women) placed 1 g of dentifrice composition on a toothbrush and freely performed the brushing for about 2 minutes, and evaluated a cool feeling during brushing the teeth and the strength of a fresh feel after rinsing the mouth, using the following criteria. In this respect, the decision results shown in Table 1 are each indicated by a rating which most of the 10 subjects gave.

TABLE 1

|  | | Examples | | | Comparative examples | |
| --- | --- | --- | --- | --- | --- | --- |
| Components (weight %) | | 1 | 2 | 3 | 1 | 2 |
| Erythritol (*1) | | 25 | 35 | 45 | | 40 |
| Erythritol (*2) | | | | | 40 | |
| Purified water | | 20 | 22 | 18 | 20 | 5 |
| Sodium carboxymethylcellulose | | 1.2 | 0.8 | 0.8 | 1.2 | |
| Carageenan | | | 0.4 | | | |
| Xanthan gum | | | | | | 0.2 |
| Sodium fluoride | | 0.21 | 0.21 | | | |
| Sodium monofluorophosphate | | | | 0.7 | | |
| Sorbitol | | Appropriate amount | Appropriate amount | Appropriate amount | Appropriate amount | Appropriate amount |
| Glycerin | | | | | | 20 |
| Propylene glycol | | 3 | 3 | 3 | 3 | 25 |
| Saccharin sodium | | 0.05 | 0.05 | 0.05 | 0.05 | 0.05 |
| Abrasive silica | | 10 | 10 | 15 | 10 | 3 |
| Sodium lauryl sulfate | | 1.5 | 1.5 | 1.5 | 1.5 | 1.5 |
| Perfume | | 1.2 | 1.2 | 1.2 | 1.2 | 1.2 |
| Total | | 100 | 100 | 100 | 100 | 100 |
| Storage stability | 5° C., 3 months | Excellent | Excellent | Excellent | Excellent | Poor |
| | Room temperature, 3 months | Excellent | Excellent | Excellent | Excellent | Poor |
| | 40° C., 3 months | Excellent | Excellent | Excellent | Excellent | Poor |
| Persistence of cool feeling | | Good | Excellent | Excellent | Poor | Excellent |

(*1) Erythritol having such particle size distribution that particles having sizes of less than 45 μm, 45 μm to less than 250 μm, and 250 μm to less than 300 μm account for 13 weight %, 82 weight %, and 5 weight %, respectively.
(*2) Erythritol having such particle size distribution that particles having sizes of less than 355 μm and 355 μm to less than 1,000 μm account for 6 weight % and 94 weight %, respectively.

As shown in Table 1, the use of the dentifrice compositions of Examples 1 to 3, which contained a high proportion of erythritol having a particle size of less than 355 μm, gave the result that they were excellent in the persistence of a cool feeling and had a good storage stability. The dentifrice compositions of Examples 2 and 3 were excellent in the persistence of cool feeling and also gave a good refreshing feel because they contain a higher proportion of erythritol having a particle size of less than 355 μm. On the other hand, the use of the dentifrice composition of Comparative Example 1 containing a great amount of erythritol having a large particle size gave the result that the cool feeling was not sensed. The use of the dentifrice composition of Comparative Example 2, which contained low proportions of water and binder, gave the result that the storage stability was poor.

Examples 4 to 7 and Comparative Examples 3 to 5

Preparation of Dentifrice Compositions

The dentifrice compositions of Examples 4 to 7 and Comparative Examples 3 to 5 were prepared according to the compositions shown in Table 2. In this regard, erythritol was lastly added.

<Evaluation Criteria for a Refreshing Feeling>
  Excellent: A fresh feeling in the mouth is strong.
  Good: A fresh feeling in the mouth is somewhat strong.
  Poor: A fresh feeling in the mouth is weak.
<Evaluation Criteria of a Cool Feeling>
  Excellent: The inside of the mouth is clearly felt, and a cool feeling therein persists.
  Good: A cool feeling in the mouth is slightly sensed.
  Poor: A cool feeling in the mouth is not sensed.

(2) Evaluation for Storage Stability
  The dentifrice compositions shown in Table 1 were each filled in a dentifrice tube for storage and stored at 5° C., room temperature, or 40° C. for 3 months. Then, the tube was cut open to evaluate whether or not a liquid component was separated from the dentifrice composition, using the following criteria.
<Evaluation Criteria for Storage Stability>
  Excellent: No separation of liquid is observed.
  Good: A slight separation of liquid is observed.
  Poor: An apparent separation of liquid is observed.

TABLE 2

| Components (weight %) | Examples | | | | Comparative examples | | |
| --- | --- | --- | --- | --- | --- | --- | --- |
| | 4 | 5 | 6 | 7 | 3 | 4 | 5 |
| Erythritol (*1) | 30 | 35 | 45 | 55 | 15 | 45 | |
| Erythritol (*2) | | | | | | | 45 |
| Purified water | 20 | 15 | 13 | 12 | 45 | 12 | 5 |
| Sodium carboxymethylcellulose (*3) | 0.8 | 0.6 | 0.6 | 0.5 | 1.0 | | |
| Sodium carboxymethylcellulose (*4) | | | | | | 1.0 | 1.0 |
| Carageenan | | 0.2 | 0.4 | | | | |
| Sodium hydroxyethylcellulose | 0.2 | | | 0.5 | | | |
| Sodium fluoride | 0.21 | 0.21 | | 0.21 | 0.21 | 0.21 | |
| Sodium monofluorophosphate | | | 0.7 | | | | 0.7 |
| Sorbitol | Appropriate amount | Appropriate amount | Appropriate amount | Appropriate amount | Appropriate amount | Appropriate amount | Appropriate amount |
| Propylene glycol | 3 | 3 | 3 | 3 | 3 | 3 | 3 |
| Saccharin sodium | 0.05 | 0.05 | 0.05 | 0.05 | 0.05 | 0.05 | 0.05 |
| Sodium lauryl sulfate | 1.5 | 1.5 | 1.5 | 1.5 | 1.5 | 1.5 | 1.5 |
| Abrasive silica | 20 | 15 | 10 | 10 | 10 | 10 | 10 |
| Perfume | 1.2 | 1.2 | 1.2 | 1.2 | 1.2 | 1.2 | 1.2 |
| Total | 100 | 100 | 100 | 100 | 100 | 100 | 100 |
| Refreshing feeling | Good | Excellent | Excellent | Excellent | Poor | Excellent | Good |
| Cool feeling | Good | Excellent | Excellent | Excellent | Poor | Excellent | Poor |
| Storage stability 5° C., 3 months | Excellent | Excellent | Excellent | Excellent | Excellent | Poor | Poor |
| Room temperature, 3 months | Excellent | Excellent | Excellent | Excellent | Excellent | Poor | Poor |
| 40° C., 3 months | Excellent | Excellent | Excellent | Excellent | Excellent | Poor | Poor |

(*1) Erythritol having such particle size distribution that particles having sizes of less than 3 μm, 3 μm to less than 45 μm, 45 μm to less than 250 μm, and 250 μm to less than 300 μm account for 1 weight %, 12 weight %, 82 weight %, and 5 weight %, respectively.
(*2) Erythritol having such particle size distribution that particles having sizes of less than 355 μm and 355 μm to less than 1,400 μm account for 6 weight % and 94 weight %, respectively.
(*3) Sodium carboxymethylcellulose having a degree of etherification of 0.9 and a 1% aqueous solution viscosity of 15 cps.
(*4) Sodium carboxymethylcellulose having a degree of etherification of 0.65 and a 1% aqueous solution viscosity of 30 cps.

As shown in Table 2, the use of the dentifrice compositions of Examples 4 to 7, which contained a high proportion of erythritol having a particle size of less than 355 μm and had sodium carboxymethylcellulose having a degree of etherification of 0.9 and a 1% aqueous solution viscosity of 15 cps, gave the result that the refreshing feel, cool feeling, and a long-term storage stability were excellent. The use of the dentifrice compositions of Examples 5 to 7, which contained a higher proportion of erythritol having a particle size of less than 355 μm, gave the result that the refreshing feel and cool feeling were further excellent.

On the other hand, the use of the dentifrice composition of Comparative Example 3, which had a low content of erythritol having a particle size of less than 355 μm and a high content of water, gave the result that the refreshing feel was weak. The use of the dentifrice composition of Comparative Example 4, which contained sodium carboxymethylcellulose having a degree of etherification of 0.65 and a 1% aqueous solution viscosity of 30 cps, gave the result that the long-term storage stability was poor. The use of the dentifrice composition of Comparative Example 5, which contained a sodium carboxymethylcellulose having a degree of etherification of 0.65 and a 1% aqueous solution viscosity of 30 cps gave the result that the cool feeling was not sensed because it contained a great amount of erythritol having a particle size of 355 μm or more and that the long-term storage stability was poor Examples 8 to 11 and Comparative Examples 6 to 8

The dentifrice compositions of Examples 8 to 11 and Comparative Examples 6 to 8 were prepared according to the compositions shown in Table 3. A refreshing feel, a cool feeling, and a storage stability were evaluated as described in Examples 4 to 7. The results are shown in Table 3.

TABLE 3

| Components (weight %) | Examples | | | | Comparative examples | | |
| --- | --- | --- | --- | --- | --- | --- | --- |
| | 8 | 9 | 10 | 11 | 6 | 7 | 8 |
| Erythritol (*1) | 30 | 35 | 45 | 55 | 15 | 45 | |
| Erythritol (*2) | | | | | | | 40 |
| Purified water | 20 | 15 | 13 | 18 | 45 | 12 | 5 |
| Sodium carboxymethylcellulose | 1.2 | 0.8 | 0.8 | 0.8 | 1.2 | 1.0 | 1.2 |
| Carageenan | | 0.4 | | 0.4 | | | |
| Silica (*3) | 7 | 4 | 3 | 2 | 4 | | |
| Silica (*4) | 20 | 15 | 10 | 10 | 10 | 15 | 10 |

TABLE 3-continued

|  |  | Examples | | | | Comparative examples | | |
| --- | --- | --- | --- | --- | --- | --- | --- | --- |
| Components (weight %) |  | 8 | 9 | 10 | 11 | 6 | 7 | 8 |
| Sodium monofluorophosphate | |  |  |  | 0.7 |  | 0.7 | 0.21 |
| Sorbitol | | Appropriate amount | Appropriate amount | Appropriate amount | Appropriate amount | Appropriate amount | Appropriate amount | Appropriate amount |
| Propylene glycol | | 3 | 3 | 3 | 3 | 3 | 3 | 3 |
| Saccharin sodium | | 0.05 | 0.05 | 0.05 | 0.05 | 0.05 | 0.05 | 0.05 |
| Sodium lauryl sulfate | | 1.5 | 1.5 | 1.5 | 1.5 | 1.5 | 1.5 | 1.3 |
| Perfume | | 1.2 | 1.2 | 1.2 | 1.2 | 1.2 | 1.2 | 1.2 |
| Total | | 100 | 100 | 100 | 100 | 100 | 100 | 100 |
| Refreshing feeling | | Good | Excellent | Excellent | Excellent | Poor | Excellent | Good |
| Cool feeling | | Good | Excellent | Excellent | Excellent | Poor | Excellent | Poor |
| Storage stability | 5° C., 3 months | Excellent | Excellent | Excellent | Excellent | Excellent | Poor | Poor |
|  | Room temperature, 3 months | Excellent | Excellent | Excellent | Excellent | Excellent | Poor | Poor |
|  | 40° C., 3 months | Excellent | Excellent | Excellent | Excellent | Excellent | Poor | Poor |

(*1) Erythritol having such particle size distribution that particles having sizes of less than 3 μm, 3 μm to less than 45 μm, 45 μm to less than 250 μm, and 250 μm to less than 300 μm account for 1 weight %, 12 weight %, 82 weight %, and 5 weight %, respectively.
(*2) Erythritol having such particle size distribution that particles having sizes of less than 355 μm and 355 μm to less than 1,400 μm account for 6 weight % and 94 weight %, respectively.
(*3) Silica having an oil absorption capacity of 300 mL/100 g
(*4) Silica having an oil absorption capacity of 120 mL/100 g As shown in Table 3, the use of the dentifrice compositions of Examples 8 to 11, which contained a high proportion of erythritol having a particle size of less than 355 μM and further had silica having an oil absorption capacity of 300 mL/100 g, gave the result that the refreshing feel, cool feeling, and long-term storage stability were excellent. In addition, the use of the dentifrice compositions of Examples 9 to 11, which contained a higher proportion of erythritol having a particle size of less than 355 μm, gave the result that the refreshing feel and the cool feeling were further excellent.

On the other hand, the use of the dentifrice composition of Comparative Example 6, which had a low content of erythritol having a particle size of less than 355 μm (having become less than 15% because of partial dissolution) and a high content of water, gave the result that the refreshing feeling and cool feeling were weak. The use of the dentifrice composition of Comparative Example 7, which did not contain silica having an oil absorption capacity of 300 mL/100 g, gave the result that the long-term storage stability was poor. The use of the dentifrice composition of Comparative Example 8 gave the result that the cool feeling was weak because of a great amount of erythritol having a particle size of 355 μm or more and that the long-term storage stability was poor because it did not contain silica having an oil absorption capacity of 300 mL/100 g.

Examples 12 to 15 and Comparative Examples 9 to 11

The dentifrice compositions of Examples 12 to 15 and Comparative Examples 9 to 11 were prepared according to the compositions shown in Table 4. In this regard, erythritol was lastly added. A refreshing feel and a cool feeling were evaluated as described in Examples 4 to 7, and foam sustainability was evaluated in the following manner. The results are shown in Table 4.

Evaluation of Foam Sustainability

Ten subjects (5 men and 5 women) placed 1 g of dentifrice composition on a toothbrush and freely performed the brushing for about 2 minutes, and evaluated foaming using the following criteria.

<Evaluation Criteria for Feelings on Use>
Excellent: foam is elastic and the foaming is good.
Good: foam is slightly elastic and the foaming is somewhat good.
Poor: foam is watery and the foaming is poor.

TABLE 4

|  | Examples | | | | Comparative examples | | |
| --- | --- | --- | --- | --- | --- | --- | --- |
| Components (weight %) | 12 | 13 | 14 | 15 | 9 | 10 | 11 |
| Erythritol (*1) | 25 | 35 | 45 | 55 | 10 | 45 |  |
| Erythritol (*2) |  |  |  |  |  |  | 40 |
| Purified water | 30 | 25 | 23 | 20 | 35 | 20 | 20 |
| Sodium lauryl sulfate | 1.3 | 1.3 | 1.3 | 1.3 | 1.3 | 1.3 | 1.3 |
| Xanthan gum | 0.05 | 0.1 | 0.2 | 0.15 | 0.2 |  |  |
| Sodium carboxymethylcellulose | 1.2 | 0.8 | 0.8 | 0.8 | 1.2 | 1.2 | 1.2 |
| Sodium fluoride | 0.21 | 0.21 |  |  | 0.21 | 0.21 | 0.21 |
| Sodium monofluorophosphate |  |  |  | 0.7 |  |  |  |
| Sorbitol | Appropriate amount | Appropriate amount | Appropriate amount | Appropriate amount | Appropriate amount | Appropriate amount | Appropriate amount |
| Propylene glycol | 3 | 3 | 3 | 3 | 3 | 3 | 3 |

TABLE 4-continued

|  | Examples | | | | Comparative examples | | |
| --- | --- | --- | --- | --- | --- | --- | --- |
| Components (weight %) | 12 | 13 | 14 | 15 | 9 | 10 | 11 |
| Saccharin sodium | 0.05 | 0.05 | 0.05 | 0.05 | 0.05 | 0.05 | 0.05 |
| Abrasive silica | 25 | 15 | 10 | 10 | 20 | 15 | 10 |
| Perfume | 1.2 | 1.2 | 1.2 | 1.2 | 1.2 | 1.2 | 1.2 |
| Total | 100 | 100 | 100 | 100 | 100 | 100 | 100 |
| Refreshing feeling | Good | Excellent | Excellent | Excellent | Poor | Excellent | Poor |
| Cool feeling | Good | Excellent | Excellent | Excellent | Poor | Excellent | Poor |
| Foaming | Excellent | Excellent | Excellent | Excellent | Excellent | Poor | Poor |

(*1) Erythritol having such particle size distribution that particles having sizes of less than 3 μm, 3 μm to less than 45 μm, 45 μm to less than 250 μm and 250 μm to less than 300 μm account for 1 weight %, 12 weight %, 82 weight %, and 5 weight %, respectively.
(*2) Erythritol having such particle size distribution that particles having sizes of less than 355 μm and 355 μm to less than 1,400 μm account for 6 weight % and 94 weight %, respectively.

As shown in Table 4, the use of the dentifrice compositions of Examples 12 to 15, which contained a high proportion of erythritol having a particle size of less than 355 μm and further had xanthan gum, gave the result that the refreshing feel, cool feeling, and the foaming were excellent. In addition, the use of the dentifrice compositions of Examples 13 to 15, which contained a higher proportion of erythritol having a particle size of less than 355 μm, gave the result that the refreshing feeling and cool feeling were further excellent. Further, none of the dentifrice compositions showed liquid separation in the test of storage stability at room temperature for 3 months.

On the other hand, the use of the dentifrice composition of Comparative Example 9, which had a low content of erythritol having a particle size of less than 355 μm, gave the result that the refreshing feeling and cool feeling were weak. The use of the dentifrice composition of Comparative Example 10, which did not contain xanthan gum, gave the result that the foam was watery and the foaming was poor. The use of the dentifrice composition of Comparative Example 11 gave the result that the refreshing feeling and cool feeling were weak because it contained a great amount of erythritol having a particle size of 355 μm or more and that the foam was watery and the foaming was poor because it did not contain xanthan gum.

Examples 16 to 19

The dentifrice compositions of Examples 16 to 19 and Comparative Examples 12 to 15 were prepared according to the compositions shown in Table 5. In this regard, erythritol was lastly added. A refreshing feeling and a cool feeling were evaluated as described in Examples 4 to 7, and a tooth-cleaning effect and injuriousness were evaluated in the following manner. The results are shown in Table 5.
(1) Evaluation of Removing Power on Dental Model Staining
  A strip of commercial video tape was attached to a plastic plate with the magnetic powder face on the top side, which was then fixed on a brush friction abrasion tester (HEIDON-14), followed by 250 times stroking a round-cut toothbrush having the normal hardness of bristle and a bristle length of 2 cm, on the whole of which each of the dentifrice compositions shown in Table 5 had been squeezed out, on the magnetic powder face at a load of 300 g, a brushing distance of 3 cm, and a speed of 120 rpm. In this regard, the dentifrice was again added every 50 strokes to perform the same test. Then, the rate of removal of the model staining was calculated from the following equation, and the removing power on the model staining was evaluated using the following criteria.

Rate of removal of model staining (%)=(Peeled area of magnetic powder/Area brushed by toothbrush)×100

Excellent: The rate of removal of the model staining is 70% or more.
  Good: The rate of removal of the model staining is 50% to less than 70%.
  Poor: The rate of removal of the model staining is less than 50%.
(2) Evaluation of Injuriousness to Teeth
  The RDA values of the dentifrice compositions shown in Table 5 were determined according to the RDA test, and the injuriousness thereof to the teeth was evaluated using the following criteria.
<Evaluation Criteria for Injuriousness to Teeth>
  Excellent: The RDA value is less than 150.
  Good: The RDA value is 150 to less than 250.
  Poor: The RDA value is 250 or more.
(3) Evaluation of Tooth-Cleaning Effect
  Based on the results on the removing power on the model staining and the injuriousness to teeth, a tooth-cleaning effect was evaluated by the following criteria.
<Evaluation Criteria for Tooth-Cleaning Effect>
  Excellent: The results of evaluation of the removing power and the injuriousness are "excellent", respectively.
  Good: One of the above-described results is "good", and another is "excellent".
  Poor: One or both of the above-described results are "poor".

TABLE 5

|  | Examples | | | | Comparative examples | | | |
| --- | --- | --- | --- | --- | --- | --- | --- | --- |
| Components (weight %) | 16 | 17 | 18 | 19 | 12 | 13 | 14 | 15 |
| Erythritol (*1) | 30 | 35 | 45 | 55 | 15 | 45 | 45 | |
| Erythritol (*2) | | | | | | | | 45 |
| Purified water | 27 | 25 | 18 | 20 | 40 | 20 | 20 | 20 |
| Sodium carboxymethylcellulose | 0.8 | 0.6 | 0.6 | 0.5 | 1.0 | 0.8 | 1.0 | 0.8 |
| Carageenan | | 0.2 | 0.4 | | | | 0.2 | 0.2 |

TABLE 5-continued

| Components (weight %) | Examples | | | | Comparative examples | | | |
|---|---|---|---|---|---|---|---|---|
| | 16 | 17 | 18 | 19 | 12 | 13 | 14 | 15 |
| Sodium hydroxyethylcellulose | 0.2 | | | 0.5 | | | | 0.2 |
| Anhydrous silica (*3) | 2 | | | 4 | 3 | 10 | | |
| Calcium hydrogenphosphate dehydrate (*4) | 8 | | 8 | | | | 10 | 3 |
| Calcium carbonate (*5) | | 5 | | | 8 | | | |
| Zeolite (*6) | | 5 | 4 | | | | | |
| Anhydrous silica (*7) | | | | 8 | | | | |
| Sorbitol | Appropriate amount | Appropriate amount | Appropriate amount | Appropriate amount | Appropriate amount | Appropriate amount | Appropriate amount | Appropriate amount |
| Propylene glycol | 3 | 3 | 3 | 3 | 3 | 3 | 3 | 3 |
| Saccharin sodium | 0.05 | 0.05 | 0.05 | 0.05 | 0.05 | 0.05 | 0.05 | 0.05 |
| Sodium lauryl sulfate | 1.5 | 1.5 | 1.5 | 1.5 | 1.5 | 1.5 | 1.5 | 1.5 |
| Perfume | 1.2 | 1.2 | 1.2 | 1.2 | 1.2 | 1.2 | 1.2 | 1.2 |
| Total | 100 | 100 | 100 | 100 | 100 | 100 | 100 | 100 |
| Refreshing feeling | Good | Excellent | Excellent | Excellent | Poor | Excellent | Excellent | Poor |
| Cool feeling | Good | Excellent | Excellent | Excellent | Poor | Excellent | Excellent | Poor |
| Removing power on model staining | Excellent | Excellent | Excellent | Excellent | Excellent | Excellent | Poor | Poor |
| Injuriousness to teeth | Excellent | Excellent | Excellent | Excellent | Excellent | Poor | Excellent | Excellent |
| Tooth-cleaning effect | Excellent | Excellent | Excellent | Excellent | Excellent | Poor | Poor | Poor |

(*1) Erythritol having such particle size distribution that particles having sizes of less than 3 μm, 3 μm to less than 45 μm, 45 μm to less than 250 μm, and 250 μm to less than 300 μm account for 1 weight %, 12 weight %, 82 weight %, and 5 weight %, respectively.
(*2) Erythritol having such particle size distribution that particles having sizes of less than 355 μm and 355 μm to less than 1,400 μm account for 6 weight % and 94 weight %, respectively.
(*3) Average particle size: 5 μm, RDA value: 180.
(*4) Average particle size: 15 μm, RDA value: 100.
(*5) Average particle size: 12 μm, RDA value: 110.
(*6) Average particle size: 6 μm, RDA value: 200.
(*7) Average particle size: 8 μm, RDA value: 100.

As shown in Table 5, the use of the dentifrice compositions of Examples 16 to 19, which contained a high proportion of erythritol having a particle size of less than 355 μm and further had powders with different polishing powers, gave the result that the refreshing feeling and tooth-cleaning effect were excellent. In addition, the use of the dentifrice compositions of Examples 17 to 19, which contained a higher proportion of erythritol having a particle size of less than 355 μm, gave the result that the refreshing feeling was further excellent. Further, none of the dentifrice compositions showed liquid separation in the test of storage stability at room temperature for 3 months.

On the other hand, the use of the dentifrice composition of Comparative Example 12, which had a low content of erythritol having a particle size of less than 355 μm, gave the result that the refreshing feeling was weak. The use of the dentifrice composition of Comparative Example 13, which contained only a powder with a high polishing power, gave the result that the injuriousness to teeth was high and therefore the tooth-cleaning effect was poor. The use of the dentifrice composition of Comparative Example 14, which contained only a powder with a low polishing power, gave the result that the removing power on dental model staining was poor and therefore the tooth-cleaning effect was poor. The use of the dentifrice composition of Comparative Example 15 gave the result that the refreshing feel and cool feeling were weak because it contained a great amount of erythritol having a particle size of 355 μm or more and that the removing power on dental model staining was poor and the tooth-cleaning effect was poor because it had a low content of polishing powder.

The invention claimed is:

1. A dentifrice composition comprising:
  (A) 15 to 60 weight % of erythritol as a powder having a particle size of less than 355 μm;
  (B) 12 to 40 weight % of water; and
  (C) 0.6 to 3 weight % of at least one binder selected from the group consisting of sodium alginate, sodium carboxymethylcellulose having a degree of etherification of from 0.8 to 1.5, carrageenan, xanthan gum, sodium polyacrylate, hydroxyethyl cellulose, hydroxypropyl cellulose, pectin, tragacanth gum, acacia gum, guar gum, karaya gum, locust bean gum, gellan gum, tamarind gum, psyllium sead gum, polyvinyl alcohol, sodium chondroitin sulfate, and methoxyethylene-maleic anhydride copolymer
  wherein said erythritol is dispersed in a powder state.

2. A dentifrice composition prepared by blending:
  (A) 25 to 60 weight % of erythritol having a particle size of less than 355 μm;
  (B) 12 to 30 weight % of water; and
  (C) 0.6 to 3 weight % of at least one binder selected from the group consisting of sodium alginate, sodium carboxymethylcellulose having a degree of etherification of from 0.8 to 1.5, carrageenan, xanthan gum, sodium polyacrylate, hydroxyethyl cellulose, hydroxypropyl cellulose, pectin, tragacanth gum, *acacia* gum, guar gum, karaya gum, locust bean gum, gellan gum, tamarind gum, psyllium sead gum, polyvinyl alcohol, sodium chondroitin sulfate, and methoxyethylene-maleic anhydride copolymer
  wherein said erythritol is dispersed in a powder state.

3. A dentifrice composition according to claim 1, wherein said component (C) is comprised of one or more binders.

4. A dentifrice composition according to claim 1, wherein said binder comprises at least sodium carboxymethylcellulose having a degree of etherification of 0.8 to 1.5.

5. A dentifrice composition according to claim 4, comprising 0.05 to 2 weight % of carboxymethylcellulose having a degree of etherification of 0.8 to 1.5.

6. A dentifrice composition according to claim 1, wherein said binder comprises at least 0.01 to 0.5 weight % of xanthan gum.

7. A dentifrice composition comprising:
(A) 15 to 60 weight % of erythritol having a particle size of less than 355 μm;
(B) 12 to 40 weight % of water;
(C) 0.6 to 3 weight % of at least one binder selected from the group consisting of sodium carboxymethylcellulose, xanthan gum, and carrageenan; and
(D) 0.5 to 10 weight % of silica having an oil absorption capacity of 200 to 400 mL/100 g,
wherein said erythritol is dispersed in a powder state.

8. A dentifrice composition according to claim 1, further comprising 5 to 20 weight % of (E) a polishing powder.

9. A dentifrice composition according to claim 8, wherein the polishing powder (E) comprises (E1) a polishing powder having an average particle size of 1 to 10 μm and an RDA value of 150 to 300 and (E2) a polishing powder having an average particle size of 5 to 20 μm and an RDA value of 50 to 150.

10. A dentifrice composition of claim 1, prepared by blending:
(A) 20 to 60 weight % of erythritol having a particle size of less than 355 μm;
(B) 12 to 40 weight % of water; and
(C) 0.6 to 3 weight % of said at least one binder.

11. A dentifrice composition of claim 1, wherein said erythritol is prepared by pulverizing crystalline erythritol.

12. A dentifrice composition of claim 1, wherein said composition is prepared by introducing said erythritol into the final step of production.

13. A dentifrice composition of claim 1, wherein said binder is present in an amount of 0.8 to 3 wt. %.

14. A dentifrice composition of claim 1, wherein said erythritol has a particle size of 45 μm to less than 355 μm.

15. A dentifrice composition of claim 1, wherein said erythritol is present in an amount of from 25 to 50 wt. %.

16. A dentifrice composition of claim 1, further comprising a foaming agent.

17. A dentifrice composition of claim 16, wherein said foaming agent is an anionic surfactant in an amount of 0.8 to 1.8 wt. %.

18. A dentifrice composition of claim 16, wherein said foaming agent is a sodium alkylsulfate and said binder comprises 0.01 to 0.5 wt. % of xanthan gum.

19. A dentifrice composition of claim 7, wherein said binder comprise (C) comprises at least one sodium carboxymethylcellulose.

* * * * *

UNITED STATES PATENT AND TRADEMARK OFFICE
CERTIFICATE OF CORRECTION

PATENT NO. : 8,961,938 B2
APPLICATION NO. : 11/512326
DATED : February 24, 2015
INVENTOR(S) : Kazuhiko Kato Page 1 of 1

It is certified that error appears in the above-identified patent and that said Letters Patent is hereby corrected as shown below:

In the Claims

Column 18, line 23: "binder comprise (C) comprises" should read --binder (C) comprises--

Signed and Sealed this
Seventh Day of July, 2015

Michelle K. Lee
*Director of the United States Patent and Trademark Office*